(12) United States Patent
Seyfried et al.

(10) Patent No.: US 7,835,601 B2
(45) Date of Patent: Nov. 16, 2010

(54) DEVICE FOR GENERATING A LASER LIGHT BEAM

(75) Inventors: Volker Seyfried, Nussloch (DE); Rafael Storz, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 89 days.

(21) Appl. No.: 11/871,389

(22) Filed: Oct. 12, 2007

(65) Prior Publication Data

US 2008/0095200 A1  Apr. 24, 2008

Related U.S. Application Data

(62) Division of application No. 11/011,475, filed on Dec. 14, 2004, now abandoned.

(60) Provisional application No. 60/532,672, filed on Dec. 23, 2003.

(30) Foreign Application Priority Data

Dec. 15, 2003 (DE) ............... 103 59 012
Dec. 22, 2003 (DE) ............... 103 61 177

(51) Int. Cl.
  *G02B 6/28* (2006.01)
  *G02B 6/36* (2006.01)
  *H01S 3/30* (2006.01)
  *H01S 3/10* (2006.01)

(52) U.S. Cl. ............... 385/14; 385/92; 372/3; 372/23

(58) Field of Classification Search ............ 385/14, 385/15, 24, 88–94; 372/6, 23
See application file for complete search history.

(56) References Cited

U.S. PATENT DOCUMENTS

| 5,771,325 | A | 6/1998 | Neuberger et al. |
| 6,222,961 | B1 | 4/2001 | Engelhardt et al. ............ 385/31 |
| 6,462,345 | B1 * | 10/2002 | Simon et al. ............ 250/458.1 |
| 7,044,654 | B2 | 5/2006 | Nakanishi et al. ............ 385/88 |

FOREIGN PATENT DOCUMENTS

| DE | 196 33 185 | 10/1997 |
| DE | 19633185 | 10/1997 |

OTHER PUBLICATIONS

Thorlabs Inc: 'Online!, XP002310416, Aug. 29, 2003, pp. 364-373.
Thorlabs Inc: "Thorlabs Inc Catalogue Volume 15", 2002, XP002310417, pp. 283-286 and 299-302.
Profile Optische Systeme GmbH "Operating instruction PRO 8000/ PRO 800 Mainframe" Mar. 1998, pp. 1-4 and 8,9,11.
Thorlabs Inc: 'Online!, XP002310416, Aug. 29, 2003, pp. 364-373.
Thorlabs Inc: "Thorlabs Inc Catalogue Volume 15", 2002, XP002310417, pp. 283-302.
Profile Optische Systeme GmbH "Operating instruction PRO 8000 / PRO 800 Mainframe" Mar. 1998, pp. 1-4 and 8-11.

* cited by examiner

*Primary Examiner*—Kevin S Wood
(74) *Attorney, Agent, or Firm*—Leydig, Voit & Mayer, Ltd.

(57) ABSTRACT

A device for generating a laser light beam includes a module. The module includes at least one laser light source, and a mechanical, an electrical and/or an optical interface defined towards an outside of the module.

19 Claims, 3 Drawing Sheets

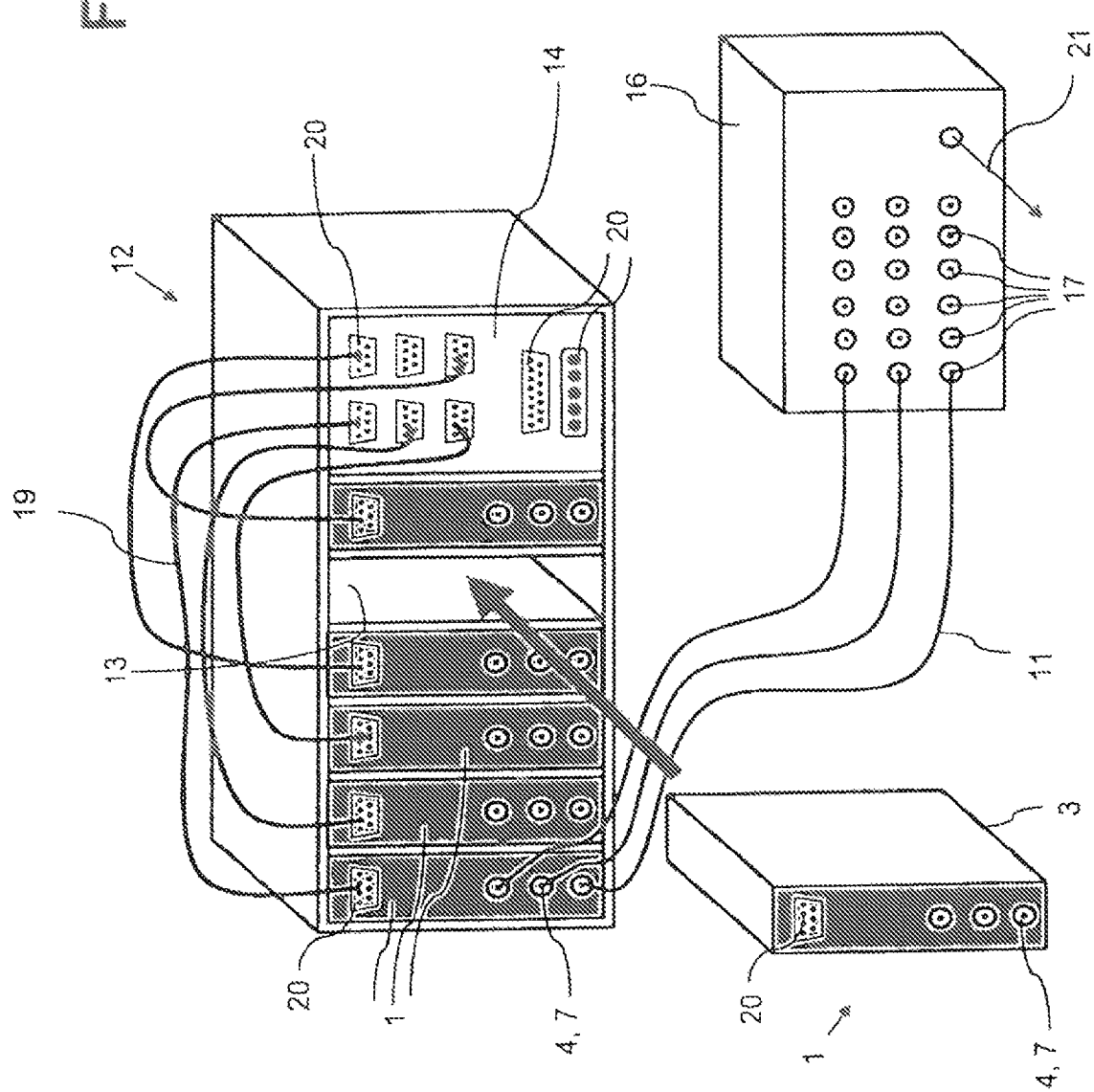

DEVICE FOR GENERATING A LASER LIGHT BEAM

This application is a divisional of U.S. Ser. No. 11/011,475, filed Dec. 14, 2004, which claims priority to U.S. Provisional Application No. 60/532,672, filed Dec. 23, 2003, German patent application DE 103 61 177.0, filed Dec. 22, 2003, and German patent application DE 103 59 012.9, filed Dec. 15, 2003. The subject matter of each of the above applications is hereby incorporated by reference.

The present invention relates to a device for generating a laser light beam, particularly an illuminating light beam for a preferably confocal scanning microscope, having at least one source of laser light.

BACKGROUND

A number of variants of devices for generating a laser light beam have been known in actual practice for years. Merely by way of an example, mention is made here of German patent DE 196 33 185 C2, which discloses a polychromatic point light source for a laser scanning microscope. Here, the radiation from a total of four sources of laser light is coaxially combined by means of a recombiner unit. Via an appropriate connection, an optical fiber leads to a laser scanning microscope, where the recombined laser light beam is coupled in with several wavelengths or with several laser lines in the form of a light point source.

The prior-art devices are problematic because the sources of laser light employed often differ from each other in terms of their mode of operation and they usually come from different manufacturers. Moreover, the sources of laser light often have different physical dimensions, in addition to which they have different electrical specifications, which makes it extremely difficult for the user to individually compose a laser light beam comprising several laser lines of individual sources of laser light. Consequently, adding a new source of laser light to an existing system or even merely replacing a single source of laser light entails a great deal of effort and usually can only be done by trained personnel. It is likewise problematic that, when a source of laser light is replaced, it is generally necessary to replace not only the laser light source itself, but also mechanical parts, optical filters, electrical interfaces, power packs, etc.

Particularly in conjunction with the illumination configuration found in confocal microscopy, in extreme cases, it is even unavoidable that the confocal microscope or at least parts of it will have to be sent to the manufacturer. In any case, however, a special service call by the device manufacturer will certainly become necessary for maintenance and retrofitting work.

Especially large-scale imaging facilities often tend to have several identical or similar confocal microscopes but these are frequently equipped with different sources of laser light. Then, it is frequently the case that only a very specific confocal microscope is suitable for a specific experiment since only that microscope has the laser light sources needed for the experiment in question. In actual practice, this often leads to certain bottlenecks in the utilization of the microscopes, particularly when several experiments are supposed to be carried out at the same time which, due to the concrete requirements made in terms of the illumination, need the same confocal microscope. It is also often the case that, for a particular observation, an inverted microscope is needed but the requisite combination of laser light sources is only available in an upright microscope. The retooling of the microscope that is then necessary entails a considerable expenditure of time and effort on the part of the user.

SUMMARY OF THE INVENTION

It is an object of the present invention to provide a device for generating a laser light beam in such a way that the laser light beam can be changed with maximum flexibility and without the need for special knowledge and so that its spectral composition can be individually selected in a simple manner.

The present invention provides a device for generating a laser light beam, such as an illuminating light beam for a preferably confocal scanning microscope, having at least one laser light source, characterized in that that the laser light sources, either individually or combined in groups, form a module that has mechanical and/or electrical and/or optical interfaces that are defined towards the outside.

According to the invention, it was recognized that there is a growing tendency towards modular device units which can be employed by users in a simple manner without entailing a lot of retooling or maintenance work. In this context, it was also recognized that special importance is now ascribed to high flexibility and adaptability to the special wishes and requirements of the user. Finally, it was recognized that such flexibility can be attained in that the sources of laser light— either individually or combined in groups—are set up in modular form, whereby the individual modules have mechanical and/or electrical and/or optical interfaces that are defined towards the outside. With such a modular set-up, a user of a confocal microscope, for example, only needs to select those laser modules that match her/his illumination requirements and she/he can then connect them to the microscope via the interfaces that are defined towards the outside within the shortest of time and without special knowledge.

BRIEF DESCRIPTION OF THE DRAWINGS

There are various ways to implement and refine the teaching of the present invention in an advantageous manner. The present invention is elaborated upon below based on exemplary embodiments with reference to the drawings. The drawings show the following.

DETAILED DESCRIPTION

Figure 1:
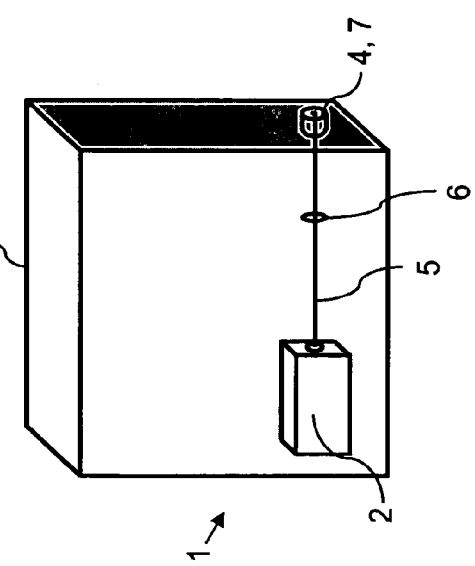
FIG. 1—a schematic depiction of a first embodiment of a device according to the invention for generating a laser light beam, with a module having at least one source of laser light.

In a preferred embodiment, there is a docking station with slots into which the individual modules are inserted or slid, whereby the modules can be arranged next to each other and/or above each other inside the docking station. For special applications, the docking station could also be configured with just one slot that accommodates one single module.

The module could have a housing that then defines the module dimensions which are advantageously adapted to the size of the slots. With an eye towards achieving high flexibility, each individual module could be encapsulated in such a way that it forms an opto-mechanical unit which, in a simple manner, can be mechanically inserted or slid into one of the slots of the docking station.

Each module could have its own power/control unit integrated into the module. In order to attain a cost reduction as well as a low-maintenance design, however, preference is given to a central power/control unit that can be brought into contact with the individual modules. In an advantageous manner, the power/control unit can be inserted or slid into the docking station or even integrated into it. A separate arrangement of the power/control unit outside of the docking station is likewise conceivable. The power/control unit has connections for external power, control and signal lines so that the power/control unit can receive energy from the outside and external control commands can be carried out.

The electrical interface of the modules can be advantageously configured in the form of cables with plug-in connectors. Likewise conceivable are cables without plug-in connectors if it is possible to simply connect the cable with the matching part intended for this purpose.

In any case, the individual modules can be connected to the power/control unit, for example, by means of power, control and signal lines. In order to achieve a high degree of flexibility when the individual modules are inserted and exchanged, it is advantageous for the interfaces of the modules to be highly uniform, so that at least largely identical power, control and signal lines can be connected to the modules.

In an embodiment that is easy to handle and provides a good overview, the electrical interface of the modules is in the form of plug-in contacts. As the counterpart to these plug-in contacts, the slots of the docking stations could have contacting elements to mechanically receive the plug-in contacts. Here, like with the known crates often employed for standardized electronic modules, the contacting elements could be configured in such a way that all of the electrical and/or optical contacts are established to the power/control unit as soon as the module has been completely inserted into a slot.

Within the scope of an embodiment of the invention, it could be provided that the contacting elements are configured, for example, by means of a switch or by means of an encoding on electronic IP building blocks in such a way that it can be seen which modules are currently inserted into the docking station. On the basis of this information, it would then be possible to monitor the current state of the docking station and of the inserted module by means of a microcontroller.

In addition to or as an alternative to the embodiments described above for the electrical interface of the modules, it is likewise conceivable to establish the communication between the modules and the power/control unit optically via optical fibers or else by means of a radio connection. With the appropriate standardization, the transmission could be realized via a Bluetooth or wireless connection.

For purposes of attaining a high degree of compatibility, it is advantageous if all of the slots of the docking station are designed identically in terms of their dimensions and the interfaces provided, so that any desired slot is available for any module. In those cases where certain modules are to be inserted only into certain slots of the docking station, for instance, because they require a special voltage supply, then the contacting elements of certain slots can be mechanically designed in such a way that the insertion of other modules is prevented.

The presence of an optical interface that is defined towards the outside means that each module has one or more defined outputs through which the light generated inside the module by the laser light sources can exit so that it can then be further utilized in a downstream unit in a simple manner and, if possible, without needing adjustment. In a preferred embodiment, the optical outputs of the modules are plug-in connectors for optical fibers. Here, by simply mounting an optical fiber, especially a glass fiber, a connection to a unit located downstream can be established in a very simple manner. So as to facilitate the handling, it is advantageous to arrange the fiber plug on the housing of the module. In particular, the fiber plug can be integrated into the front face of the housing, which is easily accessible to the user even when the module has been inserted into a slot. With such an arrangement, it is convenient to configure the optical element in the module so that the laser light beams generated inside the module are focused onto the plug-in connector in such a way that they can be directly coupled into a mounted glass fiber. For this purpose, the appropriate focusing optical element or also the fiber plug could optionally be designed so as to be adjustable.

As an alternative to focusing the laser light beam onto the fiber plug, the laser light beam could also strike the fiber plug in collimated form inside the module. The fiber plug itself could have a focusing optical element by means of which the light can be focused onto the actual glass fiber input.

It is likewise conceivable for the defined optical interface of the module not to be formed by a fiber plug on the housing of the module, but rather for the optical fibers to run through the housing to the outside. The ends of these optical fibers could have fiber plugs that constitute an optical interface of the module. In principle, the optical interface could also be in the form of one or more windows in the housing of the module, through which the laser light beams could then exit the module. However, such an arrangement calls for an external optical element or for an optical element integrated into the housing, by means of which the laser light exiting the defined interface can be further guided.

In case several laser light sources that emit different wavelengths are arranged inside a module, it is advantageous to have a beam recombiner arrangement inside the module so that the laser light beams of the individual sources of laser light can be recombined with each other already inside the module. In this manner, only one single optical interface needs to be provided in the module to couple out the laser light. As an alternative, each individual laser light beam could be guided to the outside via its own optical interface. A combination of both arrangements is likewise conceivable, even inside a single module.

In order to generate a single laser light beam, for example, an illuminating light beam for a fluorescence microscope, the laser light beams of the individual sources of laser light of the module currently in use, that is to say, modules that have been inserted into the docking station, are advantageously guided to an external beam recombiner arrangement. This beam recombiner arrangement could comprise beam recombiners arranged in a row or in groups parallel to each other, whereby the beam recombiners could be configured as wavelength-sensitive band-edge filters. In particular, the beam recombiner arrangement could be designed such that the beam recombiners are configured to couple in a laser light beam having a wavelength of a defined wavelength range. In this context, the beam recombiner arrangement can be provided either as a separate component or else as a compatible module that, similar to the power/control unit, can be integrated into the docking station by means of appropriate electrical interfaces.

The sources of laser light used inside the modules could advantageously be, in particular, solid lasers or fiber lasers. These can provide sufficient power even when they are constructed so as to be very small, so that their use translates into an especially compact construction of the individual modules and thus of the entire system.

Within the scope of an embodiment, the properties of the individual laser light sources of the modules such as intensity, wavelength, spectral width, polarization, coherence length, etc. could be varied by means of a suitable control unit. When pulsed laser light sources are employed, it would also be possible to change the pulse timing, pulse duration, pulse form or pulse repetition rate and the like. This is done by means of appropriate interfaces in that, for example, the appertaining signals (analog and/or digital) or the data are transmitted to the individual modules. Appropriate electronic circuits for processing these signals could be provided inside the modules. Moreover, the modules could have electronic circuits to directly or indirectly stabilize the laser properties such as, for instance, sensor electronic circuits, evaluation electronic circuits, closed-loop control circuits and the like. It is likewise conceivable for the electronic circuits to inform the user via appropriate interfaces about the operating state of the individual laser light sources of a module such as, for example, operating time, temperature or power.

Particularly in order to fulfill the special requirements from actual laboratory practice, the laser light sources employed inside a module could already have been adapted to concrete applications that are frequently encountered. When it comes to confocal microscopy, an application-specific module (standard imaging module) is, for instance, a module having laser light sources that emit in the wavelengths of approximately 490 nm, 570 nm and 650 nm. Especially for fluorescence microscopy, a module could be provided with the wavelengths of approximately 440 nm, 510 nm and 690 nm as a so-called fluorescent-protein (FP) module, another module having the wavelengths of approximately 470 nm, 550 nm and 630 nm as a bleaching module and another module with the wavelengths of approximately 430 nm, 610 nm and 670 nm as a module for red dyes. With such a suitable combination of laser light sources having wavelengths that are needed for many of the same applications so as to form a single module, users can keep the work and costs for reconfiguring a microscope to a minimum.

FIG. 1 schematically shows a first embodiment of a device according to the invention for generating a laser light beam, comprising a module 1 having a laser light source 2. The dimensions of the module 1 are defined by the housing 3 that surrounds the laser light source 2. The optical interface of the module 1 is formed by a fiber plug 4 arranged on the housing 3, whereby the laser light beam 5 emitted by the laser light source 2 is focused by means of a focusing lens 6 onto the beginning of the fiber of a glass fiber cable that is to be mounted onto the fiber plug 4. For the sake of clarity, the lens 6 is shown in front of the fiber plug 4 whereby, as a matter of principle, the focusing lens 6 can also be integrated into the fiber plug 4.

In order to ensure reliable operation, the module 1 has safety mechanisms (not shown here). Concretely speaking, this is a shutter arranged at the output 7 of the module 1, this shutter ensuring that light can only exit the module 1 when the system is configured properly.

Figure 2:
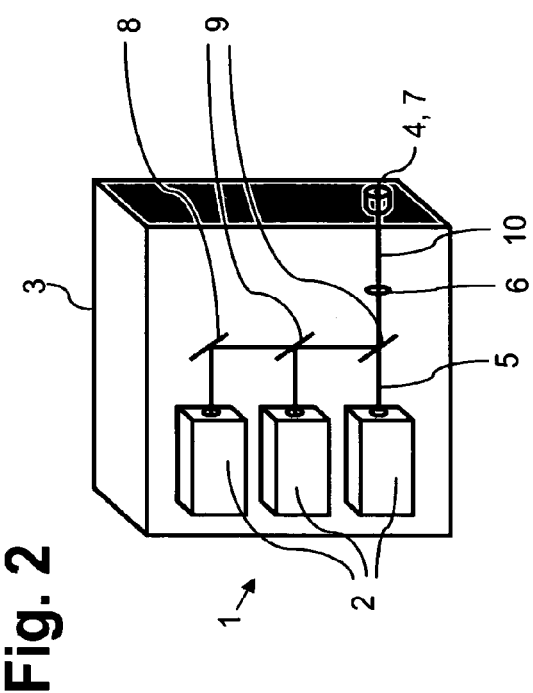
FIG. 2—a schematic depiction of a module having three sources of laser light and a joint coupling out of the light.

FIG. 2 shows a schematic depiction of a module 1 in which three laser light sources 2 are combined in groups. The three individual laser light beams 5 are recombined inside the module 1 by means of a suitable arrangement of mirrors 8 and beam recombiners 9. As already explained above in conjunction with FIG. 1, the recombined light beam 10 is focused by means of a focusing lens 6 onto a fiber plug 4 that functions as an optical interface of the module 1.

Figure 3:
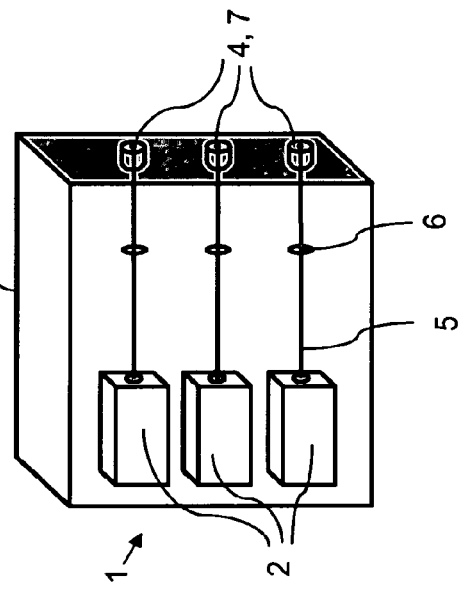
FIG. 3—a schematic depiction of a module with three sources of laser light, each having its own coupling out of the light.

FIG. 3, in turn, shows a schematic depiction of a module 1 having three laser light sources 2 combined in groups whereby, in contrast to the module 1 shown in FIG. 2, the laser light beams 5 of the individual laser light sources 2 are guided to the outside separately. Accordingly, three optical interfaces are provided on the housing 3 of the module 1.

Figure 4:
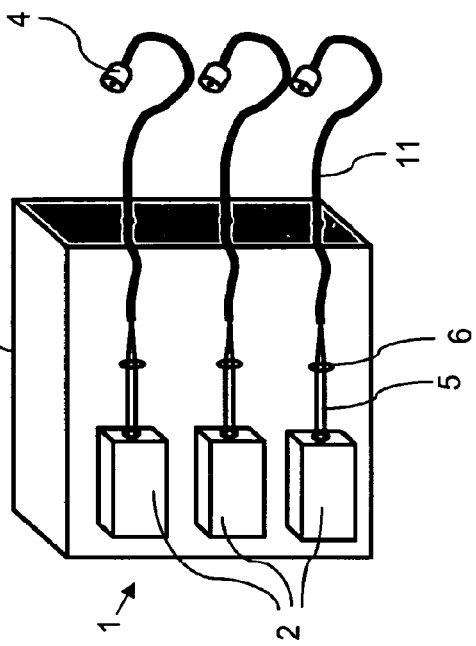
FIG. 4—a schematic depiction of a module with three sources of laser light, each having its own coupling out of the light via optical fibers.

FIG. 4 schematically shows a module 1 having three laser light sources 2 whose laser light beams 5 are transported to the outside separately via optical fibers 11. Here, the optical fibers 11 are permanently attached to the module 1 and lead from the interior of the module 1 to the outside via strain relief fiber openings on the housing 3. The optical interfaces are formed by fiber plugs 4 shaped on the fiber ends. In comparison to the embodiment according to FIG. 3, this has the advantage that it is possible to dispense with optical plug-in connectors that entail losses in power. Focusing lenses 6 then serve to couple the laser light beams 5 emitted by the laser light sources 2 into the optical fibers 11.

Figure 5:
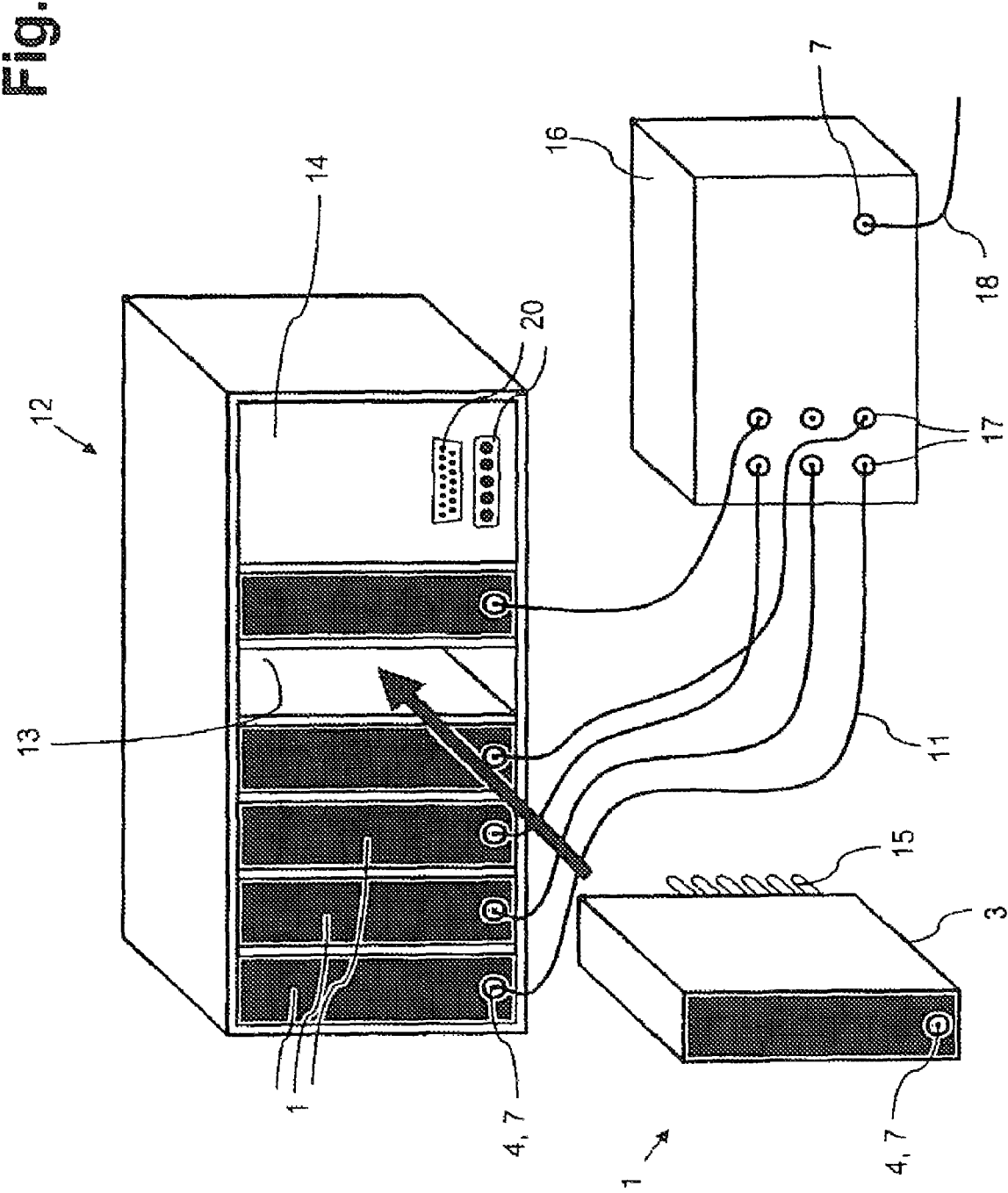
FIG. 5—a schematic depiction of several laser modules inside a docking station and FIG. 6—another embodiment of a device according to the invention, having several modules inside a docking station.

FIG. 5 shows a docking station 12 with several slots 13 into which modules 1 are inserted. The slot 13 that is located all the way to the right in the drawing serves to accommodate a power/control unit 14.

Each of the modules 1 has uniform electrical interfaces that make it possible to set up identical power, control and signal lines for each module 1. With the module 1 shown outside of the docking station 12, the electrical interface can be clearly seen as the plug-in contacts 15 that are protruding from the module 1 on the back of the housing 3. When the module 1 is inserted into the docking station 12, the appertaining electrical contacts are automatically closed by contacting elements arranged on the slots 13.

The light exiting from the individual modules 1 is guided via optical fibers 11 with plugs 4 to an external beam recombiner arrangement 16. Inside this beam recombiner arrangement 16, there are beam recombiners which are arranged and configured in such a way that each input 17 of the beam recombiner arrangement 16 serves to couple in a laser light beam 5 having a wavelength of a defined wavelength range. Consequently, a user merely has to assign the optical fibers 11 coming from the modules 1 to the correct inputs 17 of the beam recombiner arrangement 16 according to the transported wavelengths. Inside the beam recombiner arrangement 16, the laser light beams 5 coupled in via the inputs 17 are automatically recombined and then guided from an output 7 via a corresponding broadband glass fiber 18 to an application, for example, a confocal microscope. Upstream from the output 7 of the beam recombiner arrangement 16, there is an AOTF (acousto-optical tunable filter) by means of which the intensity of the individual wavelengths can be adjusted. Moreover, the beam recombiner arrangement 16 has a safety shutter located upstream from the output 7.

Some of the modules 1 shown only differ from each other in terms of a few details, for instance, their maximum achievable intensity or the control features that are present. A module 1 can also have a laser light source 2 with defined properties as the continuous laser light source 2 while another module 1 has a laser light source 2 with properties of a pulsed laser light source 2. Then, the user can chose the module 1 that is the simplest one for her/his actual requirements, thereby saving costs and time. Thus, for instance, she/he could select a module 1 that generates the wavelength 490 nm at a power of 5 mW instead of a module 1 that generates the same wavelength at a power of 20 mW.

In the example presented here, the modules 1 are selected in such a way that the distance between two wavelengths of the docking station 12 completely fitted with modules 1 is smaller than or equal to about 30 nm in each case. As a result, a proper selection of the correct excitation wavelengths can optimally excite practically any fluorescent dye since the maximum distance of the "correct" wavelength to the excitation maximum of the dye is 15 nm at the maximum. This is less than the 20 nm to 30 nm of the typical width of an excitation maximum. Consequently, with the docking station 12 completely fitted with modules 1, the user can record the excitation spectra of the dyes one point at a time, whereby the measuring points for the various wavelengths can be connected or interpolated. Such excitation spectra, which are punctiform with respect to the wavelength, can be recorded individually or linewise or imagewise for each pixel, and can then be further processed in a suitable manner. In the embodiment given, the distance of the wavelengths is also equidistant, so that an excitation spectrum can be recorded with measuring points at virtually equidistant wavelengths.

Finally, FIG. 6 schematically shows—in a manner similar to FIG. 5—a docking station 12 with several inserted modules 1. Unlike the modules 1 of FIG. 5, the electrical interfaces of the modules 1 here are not formed by plug-in contacts 15 arranged on the housing 3, but rather by cables 19 having plug-in connectors 20. By means of these cables 19, configured here as power, control and signal lines, the individual modules 1 are connected to the power/control unit 14. Moreover, plug-in connectors 20 for the power supply as well as plug-in connectors 20 with which the signal and control lines are brought in from outside can be seen in the power/control unit 14.

As a function of the number of laser light sources 2 arranged inside the module 1, each module 1 has three optical interfaces that are configured as fiber plugs 4 by means of which the light of the individual laser light sources 2 is coupled out. From the optical interface, the light is guided via optical fibers 11—as described above—to a beam recombiner arrangement 16, from where it is then conveyed, for instance, to a microscope. The latter can be, in particular, confocal scanning microscopes, semi-confocal microscopes such as, for example, line scanners, Nipkow systems or a half-tone illumination unit. Transmission to confocal endoscopes is also of great practical significance.

It should be pointed out that, by appropriately miniaturizing the laser light sources 2, the docking station 12 with the individual modules 1 and/or the beam recombiner arrangement 16 can be arranged directly on the scanning head of a confocal scanning microscope. In order to save space and reduce the weight, the power/control unit 14 should be arranged separately outside of the docking station 12. The light exiting from the beam recombiner arrangement 16 is coupled out as a free beam 21 and focused directly onto the illumination pinhole diaphragm of the confocal microscope.

In conclusion, special mention should be made of the fact that the embodiments elucidated above serve merely for purposes of describing the teaching being claimed but that the latter is not at all restricted to these embodiments.

What is claimed is:

1. A device for generating a laser light beam comprising:
   a module, the module comprising:
      at least one laser light source; and
      at least one of a mechanical, an electrical and an optical interface defined towards an outside of the module; and
   an external beam recombiner arrangement disposed in a housing separate from the module and removably coupled to the module with at least one optical fiber, the external beam recombiner including a plurality of inputs, each input being configured to receive a respective laser light beam of the at least one laser light source having a wavelength of a defined wavelength range,
   wherein the external beam recombiner arrangement includes a plurality of beam recombiners disposed therein and arranged in a row or in groups parallel to each other, and
   wherein the beam recombiners are configured to couple in the respective laser light beam corresponding to each input.

2. The device as recited in claim 1 wherein the laser light beam is an illuminating light beam for a confocal scanning microscope.

3. The device as recited in claim 1 further comprising a docking station including at least one slot configured to receive the module.

4. The device as recited in claim 1 wherein the module includes an integrated power/control unit.

5. The device as recited in claim 1 further comprising a central power/control unit configured to be brought into contact with the module.

6. The device as recited in claim 5 further comprising a docking station configured to receive the power/control unit.

7. The device as recited in claim 5 further comprising a docking station and wherein the power/control unit is integrated therein.

8. The device as recited in claim 1 wherein the module includes an electrical interface including at least one plug-in contact.

9. The device as recited in claim 8 further comprising a docking station including at least one slot configured to receive the module, the at least one slot including at least one contacting element configured to mechanically receive the at least one plug-in contact.

10. The device as recited in claim 9 wherein the at least one contacting element is configured so that when at least one of an electrical and an optical contact to the power/control unit is established when the module is completely inserted into the at least one slot.

11. The device as recited in claim 9 wherein:
   the docking station includes an integrated microcontroller; and
   the at least one contacting element is configured so that, when the module is inserted in the at least one slot, a signal is transmitted to the microcontroller.

12. The device as recited in claim 3 wherein the at least one slot includes a first and a second slot each having a respective same dimension and a respective same interface.

13. The device as recited in claim 1 further comprising an optical interface including at least one fiber plug associated with the module.

14. The device as recited in claim 1 further comprising an optical interface including at least one outlet window associated with the module.

15. The device as recited in claim 1 further comprising a docking station including at least one slot configured to receive the module, and wherein the beam recombiner arrangement is disposed in the docking station using electrical interfaces.

16. The device as recited in claim 1 wherein the at least one laser light source includes at least one of a solid and a fiber laser.

17. The device as recited in claim 1 wherein the module includes an electronic circuit configured to directly or indirectly stabilize properties of the at least one laser light source.

18. The device as recited in claim 17 wherein the electronic circuit is configured to vary the properties of the at least one laser light source, and the properties include at least one of an intensity, a wavelength, and a spectral width, a polarization, and a coherence length.

19. The device as recited in claim 17 wherein the at least one laser light source includes a pulsed laser light source, and the properties include at least one of a pulse timing, a pulse duration, a pulse form and a pulse repetition rate.

* * * * *